(12) United States Patent
Lawal et al.

(10) Patent No.: US 8,274,060 B2
(45) Date of Patent: Sep. 25, 2012

(54) ULTRAVIOLET TREATMENT CHAMBERS WITH FORCED-ORIENTATION LAMP AND SOCKET ASSEMBLY

(75) Inventors: Oliver Lawal, Fort Mill, SC (US); Seth Kacur, Beacon, NY (US)

(73) Assignee: Hanovia Limited, Slough, Berkshire (GB)

( * ) Notice: Subject to any disclaimer, the term of this patent is extended or adjusted under 35 U.S.C. 154(b) by 200 days.

(21) Appl. No.: 12/862,241

(22) Filed: Aug. 24, 2010

(65) Prior Publication Data

US 2011/0204254 A1    Aug. 25, 2011

Related U.S. Application Data

(63) Continuation-in-part of application No. PCT/US2010/035754, filed on May 21, 2010.

(60) Provisional application No. 61/180,553, filed on May 22, 2009.

(51) Int. Cl.
*A61L 2/00* (2006.01)

(52) U.S. Cl. ............... 250/455.11; 250/493.1; 250/436; 250/437; 422/22; 422/23; 422/24

(58) Field of Classification Search ............ 250/453.11, 250/454.11, 455.11, 493.1, 504 R, 428, 432 R, 250/436, 437; 422/1, 22, 23, 24
See application file for complete search history.

(56) References Cited

U.S. PATENT DOCUMENTS

| 5,166,527 | A | 11/1992 | Solymar |
| 5,780,860 | A * | 7/1998 | Gadgil et al. ............. 250/432 R |
| 6,634,902 | B1 | 10/2003 | Pirovic |
| 2006/0186782 | A1* | 8/2006 | Ciancanelli et al. ..... 313/318.01 |
| 2006/0267495 | A1* | 11/2006 | Pirovic .......................... 313/547 |
| 2007/0101867 | A1* | 5/2007 | Hunter et al. ................... 96/224 |
| 2007/0202738 | A1 | 8/2007 | Ciancanelli et al. |
| 2008/0182454 | A1* | 7/2008 | Zayas ........................... 439/617 |

OTHER PUBLICATIONS

International Search Report dated Dec. 24, 2010, PCT Application No. PCT/US2010/035754, Hanovia Limited.
Notification Concerning Transmittal of International Preliminary Report on Patentability, dated Dec. 1, 2011 in reference to PCT International Appln. No. US2010/035754 filed May 21, 2010.

* cited by examiner

*Primary Examiner* — David A Vanore
*Assistant Examiner* — Nicole Ippolito
(74) *Attorney, Agent, or Firm* — Dinsmore & Shohl, LLP

(57) ABSTRACT

A lamp mounting assembly that mounts a UV lamp within a flow control structure includes a mount assembly that mounts at an end of the flow control structure. The mount assembly includes a conductor housing receiving opening extending therethrough. A socket base structure includes a socket base and a conductor housing extending outwardly from the socket base. The conductor housing is sized to be received by the conductor housing receiving opening of the mount assembly. A lamp socket is connected to the conductor housing to allow an electrical connection between the lamp socket and a power source. The lamp socket has a lamp engaging surface arranged offset from vertical when mounted to the flow control structure.

17 Claims, 9 Drawing Sheets

ULTRAVIOLET TREATMENT CHAMBERS WITH FORCED-ORIENTATION LAMP AND SOCKET ASSEMBLY

CROSS-REFERENCE TO RELATED APPLICATIONS

This application is filed under 35 U.S.C. §111(a) as a continuation-in-part of International Patent Application No. PCT/US2010/035754, which international application designates the United States and claims the benefit of U.S. Provisional Application Ser. No. 61/180,553, filed May 22, 2009.

TECHNICAL FIELD

The present disclosure relates to ultraviolet germicidal water purification systems and, more particularly, to systems incorporating a specialized socket assembly configured to ensure optimum performance.

BACKGROUND

Ultraviolet (UV) radiation may be used in purification systems for use in cleaning of water or other fluids. The UV radiation acts to kill bacteria and germs. The purification systems may utilize a UV lamp that is connected to a power source using a lamp mounting assembly. The lamp mounting assembly may include a socket into which the UV lamp is plugged. There is a need for purification systems that provide enhanced efficacy (e.g., enhanced water disinfecting capability) and lower operational costs.

SUMMARY

In an embodiment, an ultraviolet (UV) water purification system includes a flow control structure comprising a first end, a second, opposite end and an elongated axis that passes between the first and second ends. The flow control structure includes a UV water purification chamber that receives a fluid during a purification operation. A lamp mounting assembly is configured to mount a UV lamp at least partially within the flow control structure. The lamp mounting assembly includes a mount assembly mounted at the first end of the flow control structure. The mount assembly includes a conductor housing receiving opening extending therethrough. A socket base structure includes a socket base and a conductor housing extending outwardly from the socket base. The conductor housing is received by the conductor housing receiving opening of the mount assembly. A lamp socket is connected to the conductor housing to allow an electrical connection between the lamp socket and a power source. The lamp socket has a lamp engaging surface arranged offset from 90 degrees to the elongated axis of the flow control structure. Alignment structure includes a locating pin and a pin-receiving opening sized to receive the pin. The pin-receiving opening extends into at least one of the mount assembly and the socket base structure that receives the pin to align the socket base structure and the lamp engaging surface at a predetermined rotational orientation about the elongated axis of the flow control structure. A UV lamp includes a socket connector having a socket engaging surface arranged offset from 90 degrees to the elongated axis of the flow control structure. The offset arrangements of the lamp engaging surface and the socket engaging surface cooperate when connecting the socket connector to the lamp socket to automatically align the UV lamp so that an amalgam spot of the UV lamp is located approximately at a bottom position of a circular cross-section of the UV lamp.

In another embodiment, a lamp mounting assembly that mounts a UV lamp within a flow control structure includes a mount assembly that mounts at an end of the flow control structure. The mount assembly includes a conductor housing receiving opening extending therethrough. A socket base structure includes a socket base and a conductor housing extending outwardly from the socket base. The conductor housing is sized to be received by the conductor housing receiving opening of the mount assembly. A lamp socket is connected to the conductor housing to allow an electrical connection between the lamp socket and a power source. The lamp socket has a lamp engaging surface arranged offset from vertical when mounted to the flow control structure.

In another embodiment, a UV lamp includes a socket connector having a socket engaging surface arranged offset from 90 degrees to an elongated axis of the UV lamp. The offset arrangement of the socket engaging surface cooperates with an offset arrangement of a lamp engaging surface of a lamp socket when connecting the socket connector to the lamp socket to automatically align the UV lamp so that an amalgam spot of the UV lamp is located approximately at a bottom position of a circular cross-section of the UV lamp.

BRIEF DESCRIPTION OF THE DRAWINGS

The following description of specific embodiments of the present disclosure can be best understood when read in conjunction with the following drawings, where like structure is indicated with like reference numerals and in which.

DETAILED DESCRIPTION

Embodiments described herein generally relate to UV treatment systems for treating a fluid such as water. The UV treatment systems may include a large stainless steel pipe or other flow control structure with one or more UV purification lamps mounted therein. As will be described in greater detail below, the UV treatment systems may be provided with a lamp mounting assembly that can be used to automatically orient the UV lamp at a predetermined rotational orientation about the elongated axis of the flow control structure where such orientation of the UV lamp may be required to electrically connect the UV lamp to a power source. Such a lamp mounting assembly can provide repeatable reconnection of UV lamps in the predetermined rotational orientation, which can enhance operation of the UV lamps.

Figure 1:
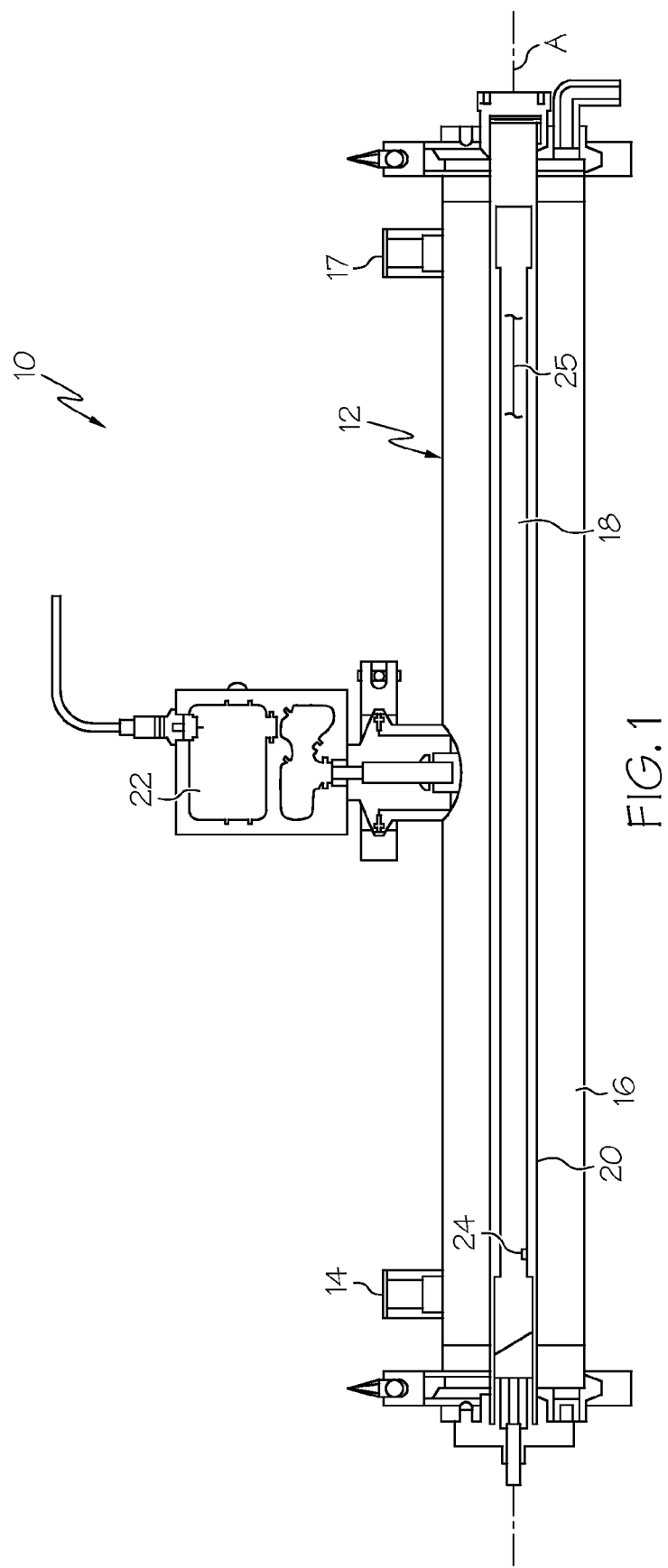
FIG. 1 is an illustration of a UV treatment chamber incorporating concepts of the present disclosure.

Referring to FIG. 1, an embodiment of a UV treatment system 10 includes a flow control structure 12 (e.g., a stainless steel pipe) including an inlet port 14 for ingress of untreated water into a UV treatment chamber 16 and an outlet port 17 for egress of treated water from the UV treatment chamber 16. An elongated axis A extends along the length of the flow control structure 12. A UV lamp 18 is located in the flow control structure 12 and is separated from the UV treatment chamber 16 by a sleeve 20. In some embodiments, the UV lamp 18 may be isolated from direct exposure to the water by one or more sleeve 20, which may be made of a material such as quartz, for example. The sleeve 20 allows the UV lamp 18 to operate optimally and also allows operators to replace the UV lamp 18 without interrupting water flow. Water that contains high levels of organics or other contaminants may require being chambered with automated internal monitoring and cleaning mechanisms. For example, a UV sensor 22 may be installed in the vicinity of the UV lamp 18 and can be used to provide an indication of lamp failure or degradation. Wipers (not shown) can also be provided to remove deposits when appropriate.

Although there are a variety of types of UV lamps that can be used in the UV treatment chamber 16, some aspects of the present disclosure may be particularly advantageous in the context of amalgam lamps. These lamps are called amalgam lamps because they contain solid amalgam spots (see element 24 of FIG. 1) on their interior surface. The amalgam spots are typically an alloy of mercury with another element, such as indium or gallium, and function to control the mercury vapor pressure of the lamp.

Without wishing to be bound by theory, the present inventors have recognized that the aforementioned components of UV treatment system 10 may introduce particular operational challenges that can be addressed by providing a specialized lamp and socket assembly. In particular, it may be desirable to force orientation of the UV lamp 18 that utilize one or more amalgam spots 24 and longitudinal off-axis conductors. More specifically, where one or more amalgam spots 24 are utilized on the interior surface of the UV lamp 18, the present inventors have recognized that, if a particular lamp is installed in a rotational orientation that would place the amalgam spot on a high point of the interior surface of the lamp, away from the bottom (6 o'clock) position of the circular cross-section of the UV lamp 18, then the one or more amalgam spots 24 are more likely to become displaced or fully or partially dislodged, particularly under the relatively high operational temperatures of the UV lamp 18. The lamp and socket assembly of the present disclosure can be utilized to ensure that the one or more amalgam spots 24 can be located approximately at the bottom (6 o'clock) position of the UV lamp 18 because a user replacing or maintaining the UV lamp 18 is forced to install a new lamp or reinstall the existing lamp in a singular state of rotational orientation. When the UV lamp 18 is installed in this manner, the amalgam spots 24 will be less likely to become displaced or dislodged and the operation of the UV lamp 18 can be enhanced.

Furthermore, the UV lamp 18 may employ one or more PTFE-coated wires that run along the length of the exterior surface of the UV lamp 18 to provide electrical contact with the filaments of the bulb. The present inventors have recognized that, if a particular lamp is installed in a rotational orientation that would place the wire in a position that would obstruct the optical path between the bulb and the UV sensor utilized to monitor the intensity of the bulb, then the sensor may tend to provide an inaccurately low indication of bulb intensity. The lamp and socket assembly of the present disclosure can also be utilized to ensure that the longitudinal wire (e.g., see element 25 representing a portion of a longitudinal wire) can be located outside of the optical path, i.e., away from the top (12 o'clock) position of the lamp because a user replacing or maintaining the UV lamp is forced to install a new lamp or reinstall the existing lamp in a singular state of rotational orientation. Installed in this manner, the longitudinal wire will be less likely to interfere with intensity monitoring.

Figure 2:
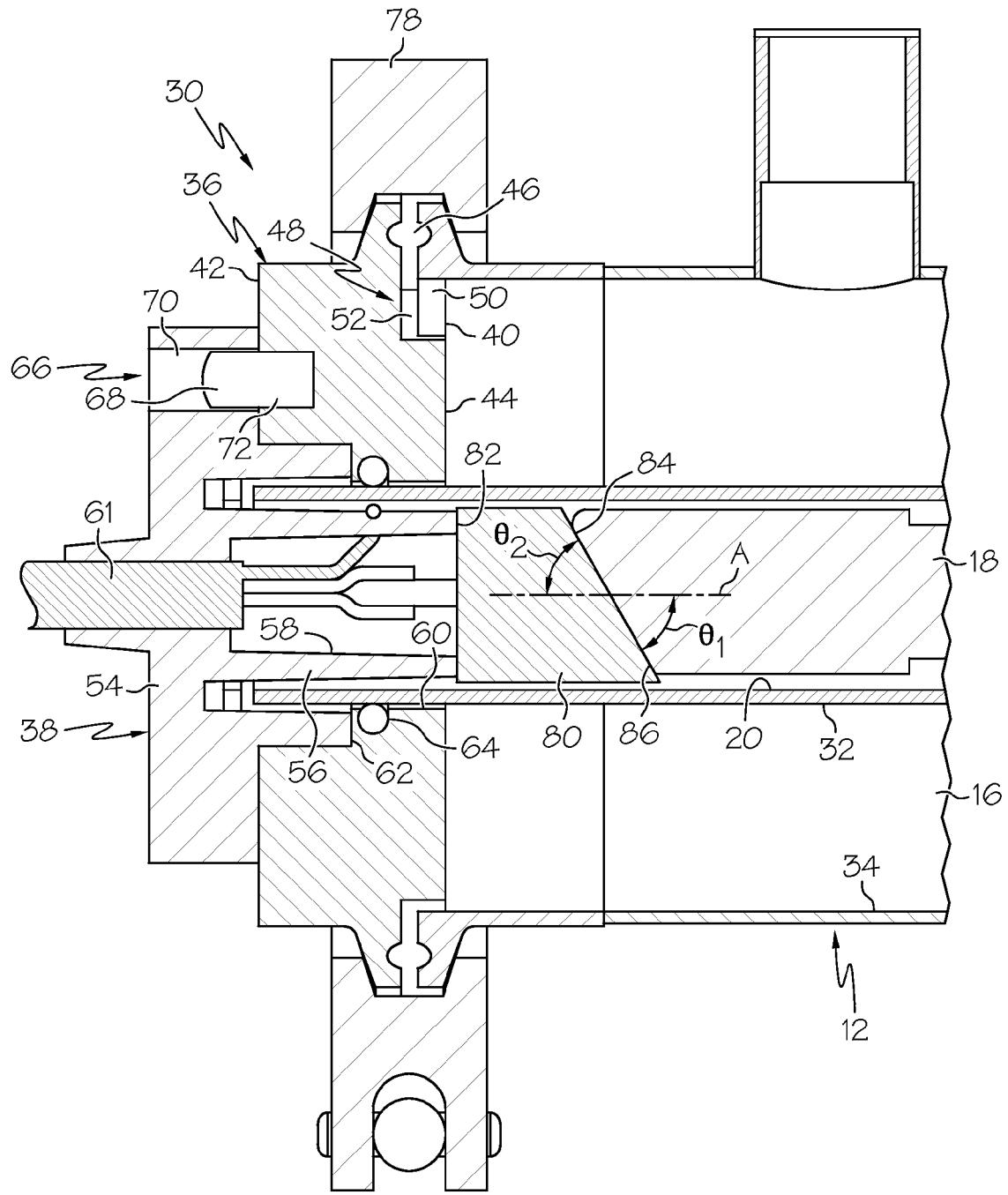
FIG. 2 is an isolated socket-end view of a UV treatment chamber incorporating concepts of the present disclosure.
Figure 3:
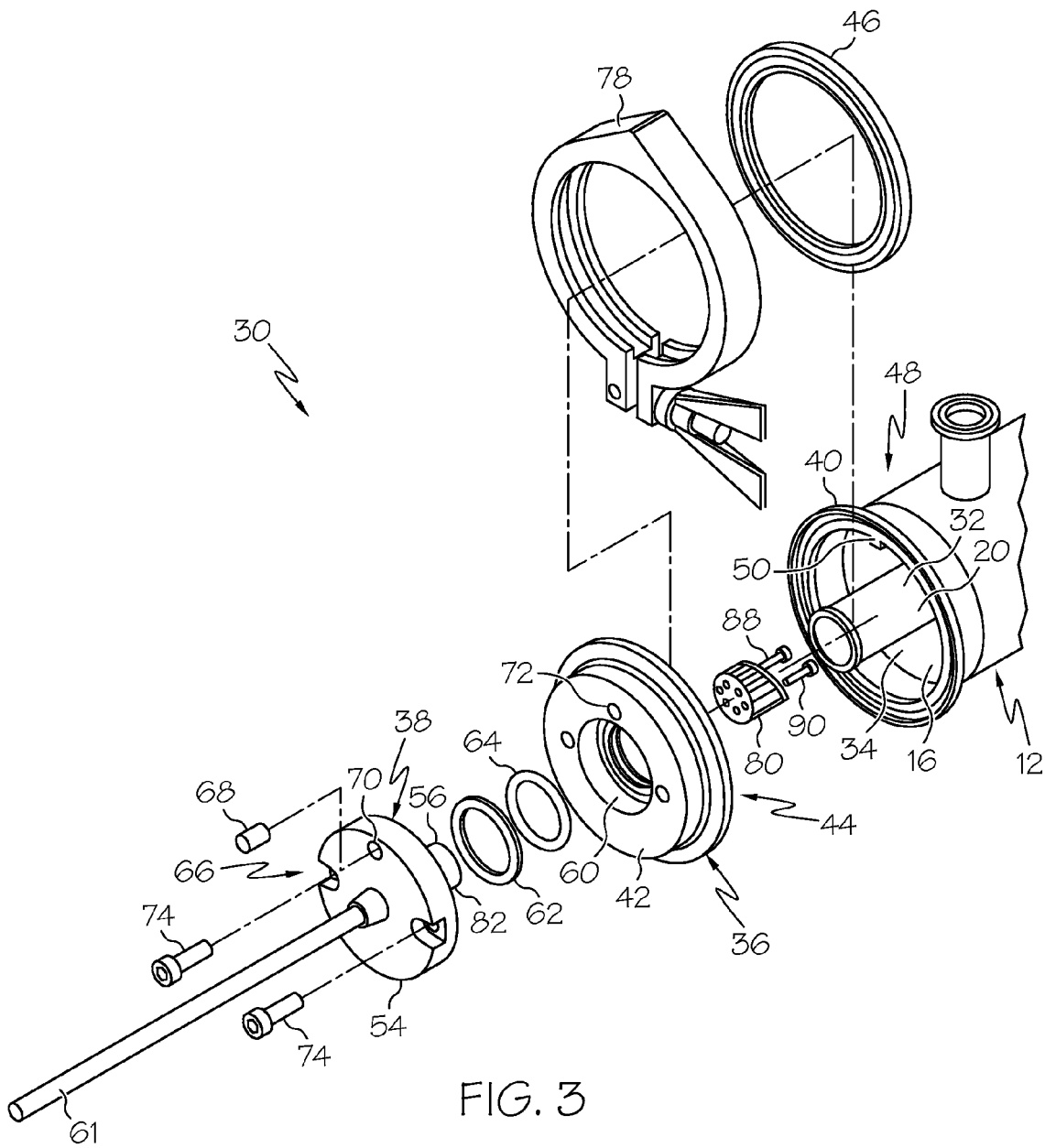
FIG. 3 is an exploded socket-end view of a UV treatment chamber incorporating concepts of the present disclosure.

More specifically, referring to FIGS. 2 and 3, a lamp mounting assembly 30 is generally used to mount the UV lamp 18 within the flow control structure 12 thereby defining the UV treatment chamber 16 located between an outer surface 32 of the sleeve 20 and an inner surface 34 of the flow control structure 12. The lamp mounting assembly 30 includes an assembly mount 36 that is used to mount and align a socket base structure 38 to an end 40 of the flow control structure 12. The assembly mount 36 includes an outer surface 42 that faces the socket base structure 38 and an inner surface 44 that faces the flow control structure 12. A sealing ring 46 may be provided for providing a fluid-tight seal between the assembly mount 36 and the flow control structure 12 when mounted thereto. An alignment structure 48 may be provided for aligning the assembly mount 36 in a predetermined angular orientation with the flow control structure 12. In the embodiment of FIGS. 2 and 3, the alignment structure 48 includes a notch 50 formed at a periphery of the flow control structure 12 and a recess 52 that is formed in the inner surface 44 of the assembly mount 36. The notch 50 of the flow control structure 12 is received within the recess 52 of the assembly mount 36 to control alignment of the assembly mount 36 when being connected to the flow control structure 12. In some embodiments, the alignment structure 48 prevents connection between the assembly mount 36 and the flow control structure 12 in any angular position other than when the notch 50 is received within the recess. In other embodiments, there may be multiple connecting alignments (e.g., more than one recess 52 and/or notch 50).

The socket base structure 38 includes a socket base 54 and a conductor housing 56 extending outwardly from the socket base 54. As can be more clearly seen by FIG. 2, the socket base 54 and conductor housing 56 include a bore 58 extending therethrough that receive conductors 61 for connecting the UV lamp 18 to a power source. The conductor housing 56 extends laterally (i.e., in the direction of the elongated axis A of FIG. 1) and is received within a conductor housing receiving opening 60 extending through the assembly mount 36. In some embodiments, a pair of sealing rings 62 and 64 may be located between the socket base structure 38 and the assembly mount 36.

An alignment structure 66 may be used to align the socket base structure 38 at a predetermined angular position relative to the assembly mount 36. In the illustrated embodiment, a locating pin 68 may be received within aligned openings 70 and 72 extending into the socket base structure 38 and the assembly mount 36, respectively. Other alignment structure arrangements may be used, such as a locating pin that extends integrally outward from either one of the assembly mount 36 and the socket base structure 38. Fasteners 74 or other connecting structures may be used to fasten or otherwise mount the socket base structure 38 to the assembly mount 36 in the predetermined angular orientation. A bracket 78 may be used to interlock the lamp mounting assembly 30 to the flow control structure 12.

A lamp socket 80 is connected to an end 82 of the conductor housing 56 thereby electrically connecting the lamp socket 80 to the power source. In some embodiments, both the end 82 of the conductor housing 56 and the lamp socket 80 connected thereto extend beyond the inner surface 44 of the assembly mount 36 and into the sleeve 20 at a location within the flow control structure 12, however, other arrangements are contemplated.

Referring particularly to FIG. 2, the lamp socket 80 and UV lamp 18 each comprise engaging surfaces 84 and 86 that, in the illustrated embodiment, are mitered to force the UV lamp 18 to adopt a fixed rotational orientation about the longitudinal lamp axis (or elongated axis A of the flow control structure) relative to the lamp socket 80. In the exemplary embodiment of FIG. 2, the engaging surface 84 is at an angle $\theta_1$ and the engaging surface 86 is at an angle $\theta_2$ to the elongated axis A. As is clearly illustrated in FIG. 2, the angles $\theta_1$ and $\theta_2$ are opposite, congruent angles, the mitered lamp engaging surface 84 defines a mitered leading edge of the lamp socket 80, and the mitered socket engaging surface 86 defines a mitered leading edge of the UV lamp 18. In some embodiments, the angles $\theta_1$ and $\theta_2$ are offset from 90 degrees to the elongated axis A of the flow control structure 12. In some embodiments, $\theta_1$ and $\theta_2$ may have approximately the same offset to the elongated axis A of the flow control structure 12. As may be appreciated, a user replacing or maintaining the UV lamp 18 is forced to install a new lamp or reinstall the existing lamp in a singular state of rotational orientation, relative to the longitudinal axis of the UV chamber.

Figure 5:
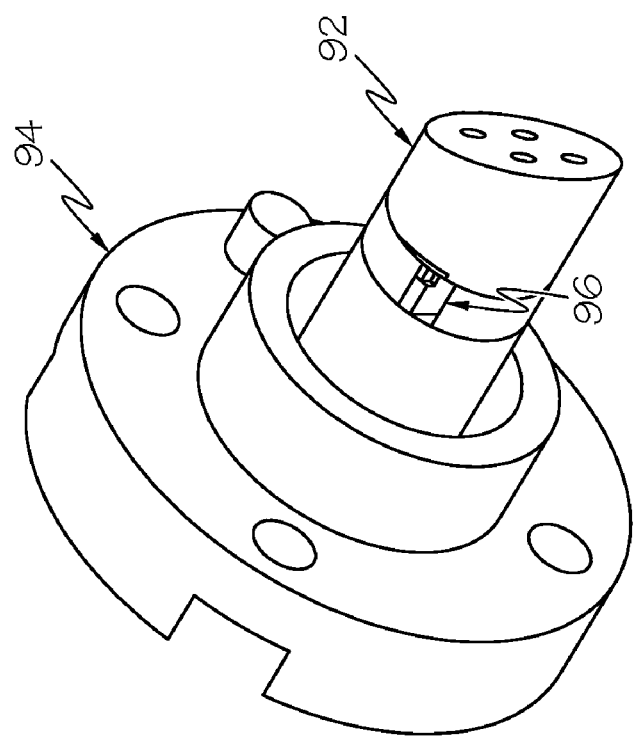
FIG. 5 is an illustration of a snap-on lamp socket and socket base according to the present disclosure.
Figure 4:
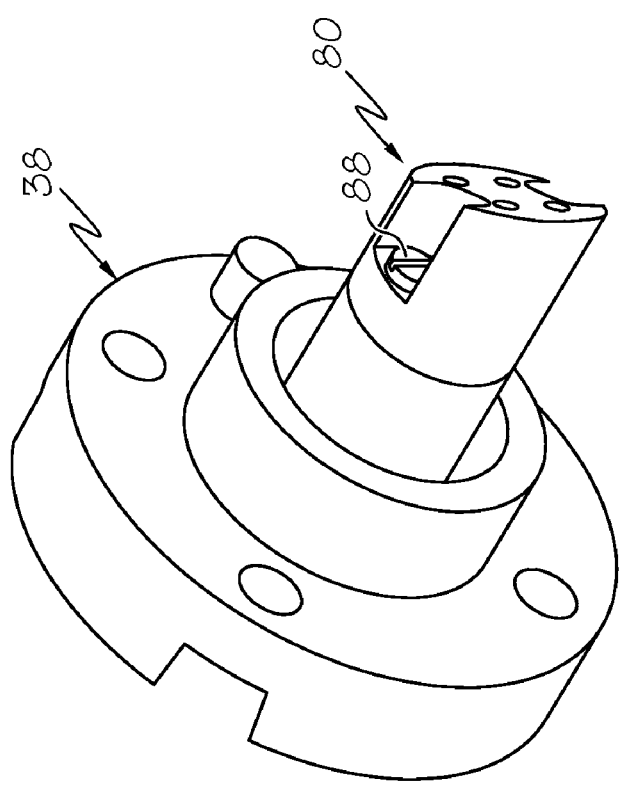
FIG. 4 is an illustration of a screw-on lamp socket and socket base according to the present disclosure.

Referring to FIG. 4, the lamp socket 80 is shown in greater detail connected to the socket base structure 38. In this illustrative embodiment, the lamp socket 80 is connected to the socket base structure 38 using fasteners 88 and 90. Referring to FIG. 5, another embodiment of a lamp socket 92 is illustrated where the lamp socket 92 is snap fit onto a socket base structure 94. In this embodiment, the lamp socket 92 and the socket base structure 94 each include cooperating interlocking structures 96 that are used to connect the lamp socket 92 to the socket base structure 94. In some embodiments, the lamp socket is removably connected to the socket base structure and the lamp socket may be retrofitted onto an existing socket base structure to provide the offset engaging surface.

Figure 6:
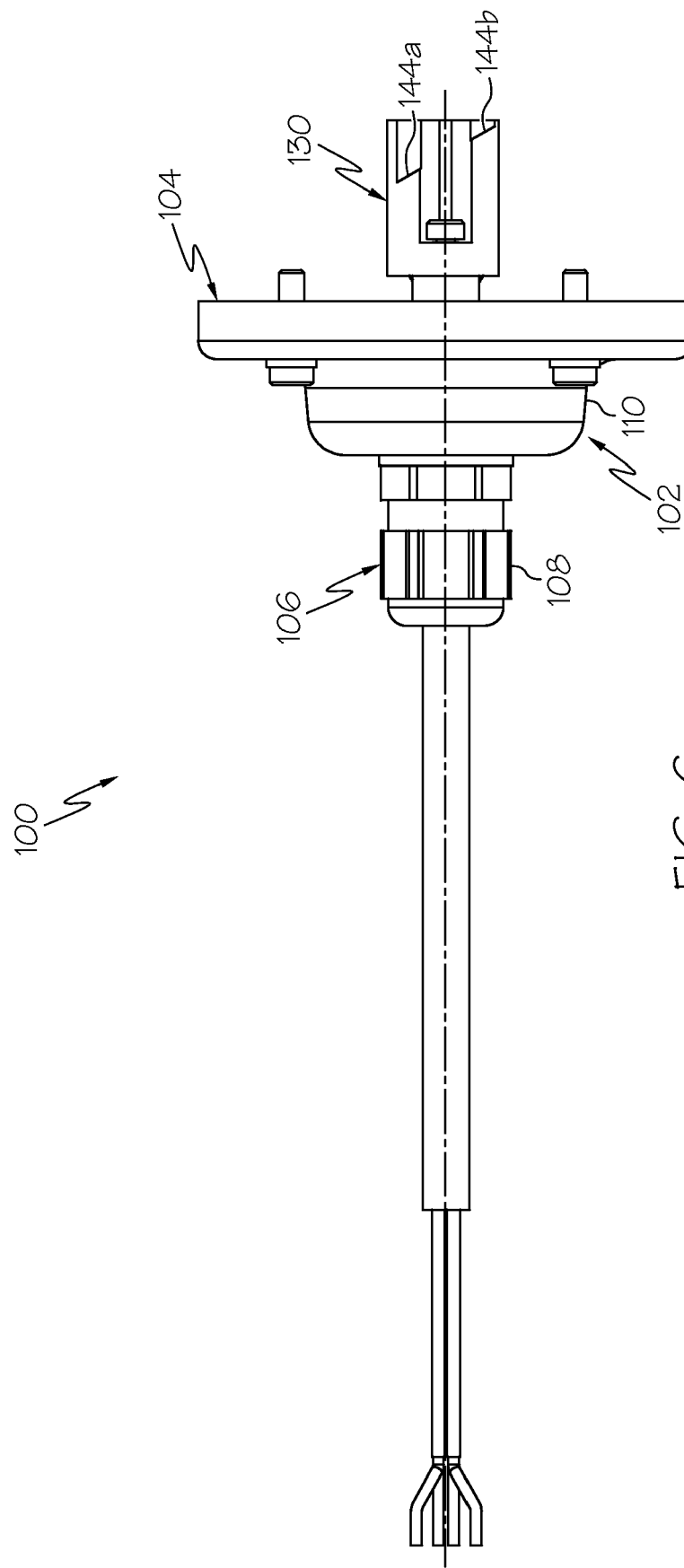
FIG. 6 is a side view of an embodiment of a lamp head assembly according to the present disclosure.
Figure 7:
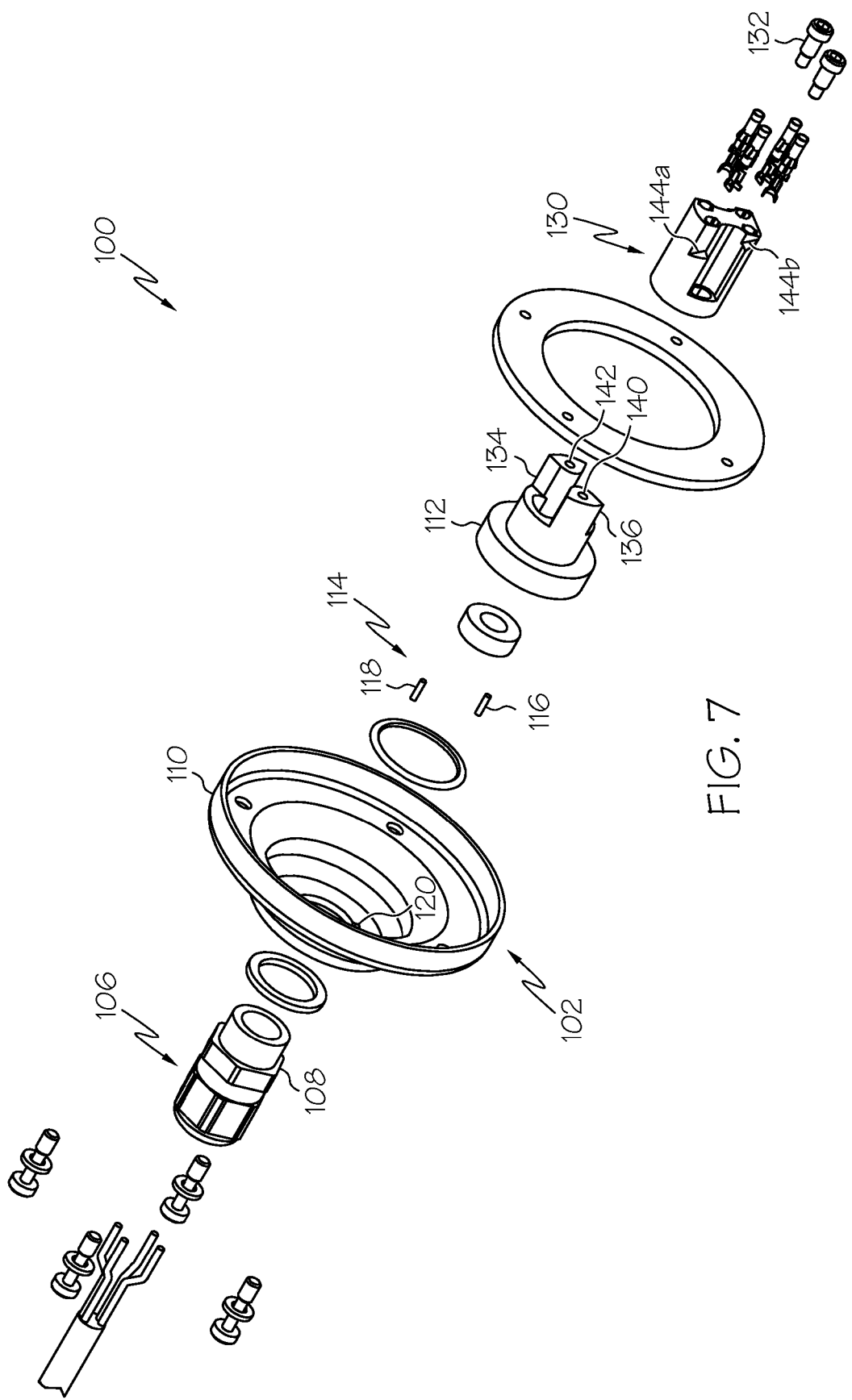
FIG. 7 is an exploded view of the lamp head assembly of FIG. 6 according to the present disclosure.
Figure 8:
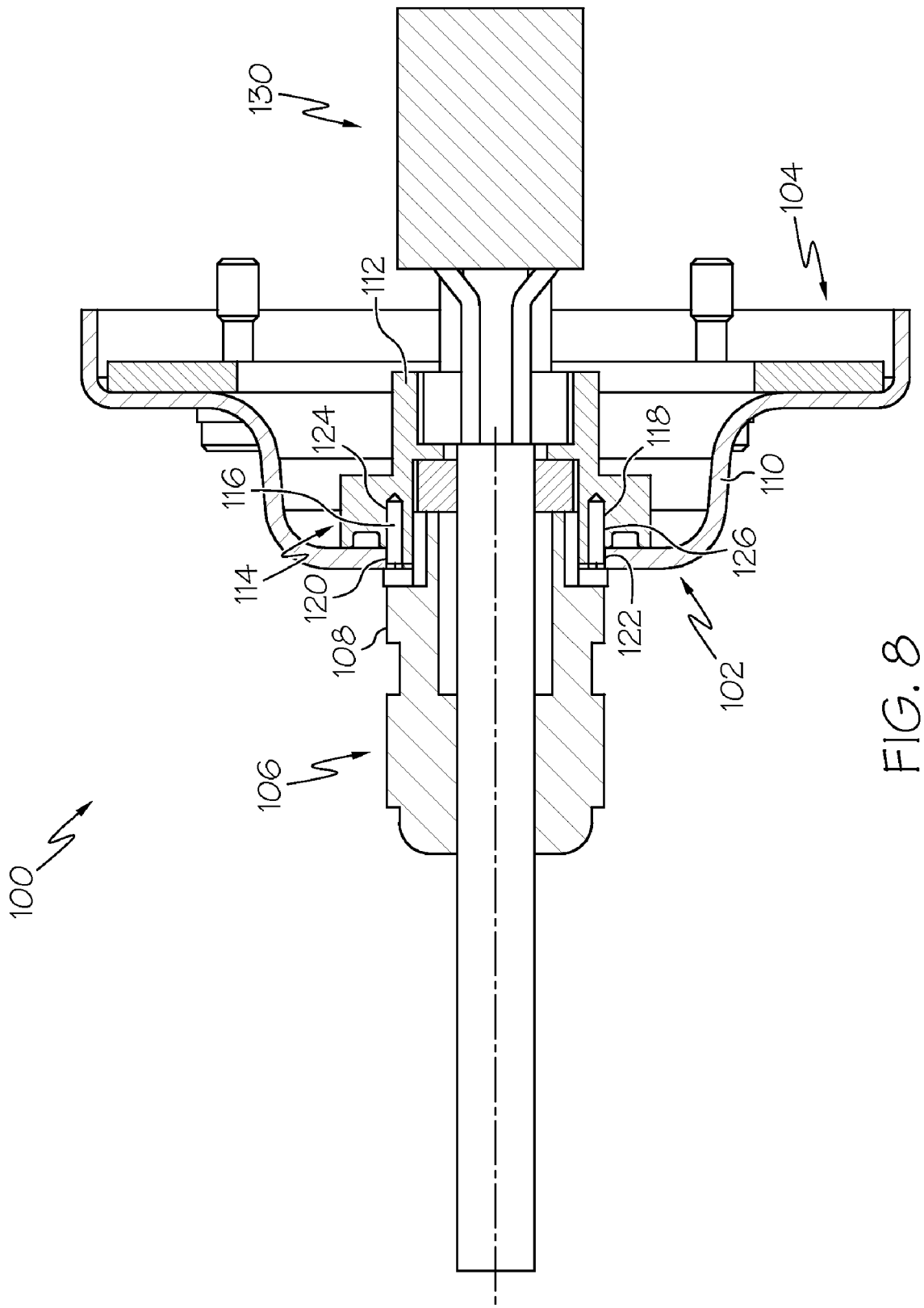
FIG. 8 is a section view of the lamp head assembly of FIG. 6 according to the present disclosure.

Referring to FIGS. 6-8, another embodiment of a lamp lead assembly 100 generally includes a socket base structure 102 that is formed by a cable gland assembly 106 and an end cap assembly 104 and a lamp socket 130. The cable gland assembly 106 includes a first cable gland member 108 that can be fit through an opening in an end cap member 110 of the end cap assembly 104 and a second cable gland member 112 that abuts the end cap assembly 104 and can be connected to the first cable gland member 108 (e.g., using a threaded connection).

Referring particularly to FIG. 8, alignment structure 114 may be provided to orient the second cable gland member 112 relative to the end cap member 110. In the illustrated embodiment, alignment pins 116 and 118 may be provided that can be press fit into slots 120 and 122 in the end cap member 110. In some embodiments, as shown by FIG. 8, the slots 120 and 122 may be offset from each other (e.g., less or greater than 180 degrees from each other). The second cable gland member 112 may include corresponding slots 124 and 126 that are sized to receive the alignment pins 116 and 118. Because the alignment pins 116 and 118 are offset from each other, the second cable gland member 112 can receive both alignment pins 116 and 118 in only one rotational orientation.

The lamp socket 130 can be connected to the second cable gland member 112 using fasteners 132 (or using a snap-fit, press-fit connection and the like). The lamp socket 130 may rest against upper planar surfaces 134 and 136 (FIG. 6) with the fasteners 132 passing through openings 140 and 142. Because the second cable gland member 112 is aligned using the alignment structure 114, the lamp socket 130 is also automatically aligned in order to connect the lamp socket 130 to the second cable gland member 112.

Referring back to FIG. 6, once the lamp lead assembly 100 is assembled as shown, the lamp socket 130 includes lamp engagement surfaces 144a and 144b. The lamp engagement surfaces 144a and 144b are both at an angle to the horizontal. In some embodiments, both lamp engagement surfaces 144a and 144b are at the same angle to the horizontal and lie in the same plane, however, they may be at different angles and/or lie in different planes. Additionally, there may be similar lamp engagement surfaces on the opposite side of the lamp socket 130.

Figure 9:
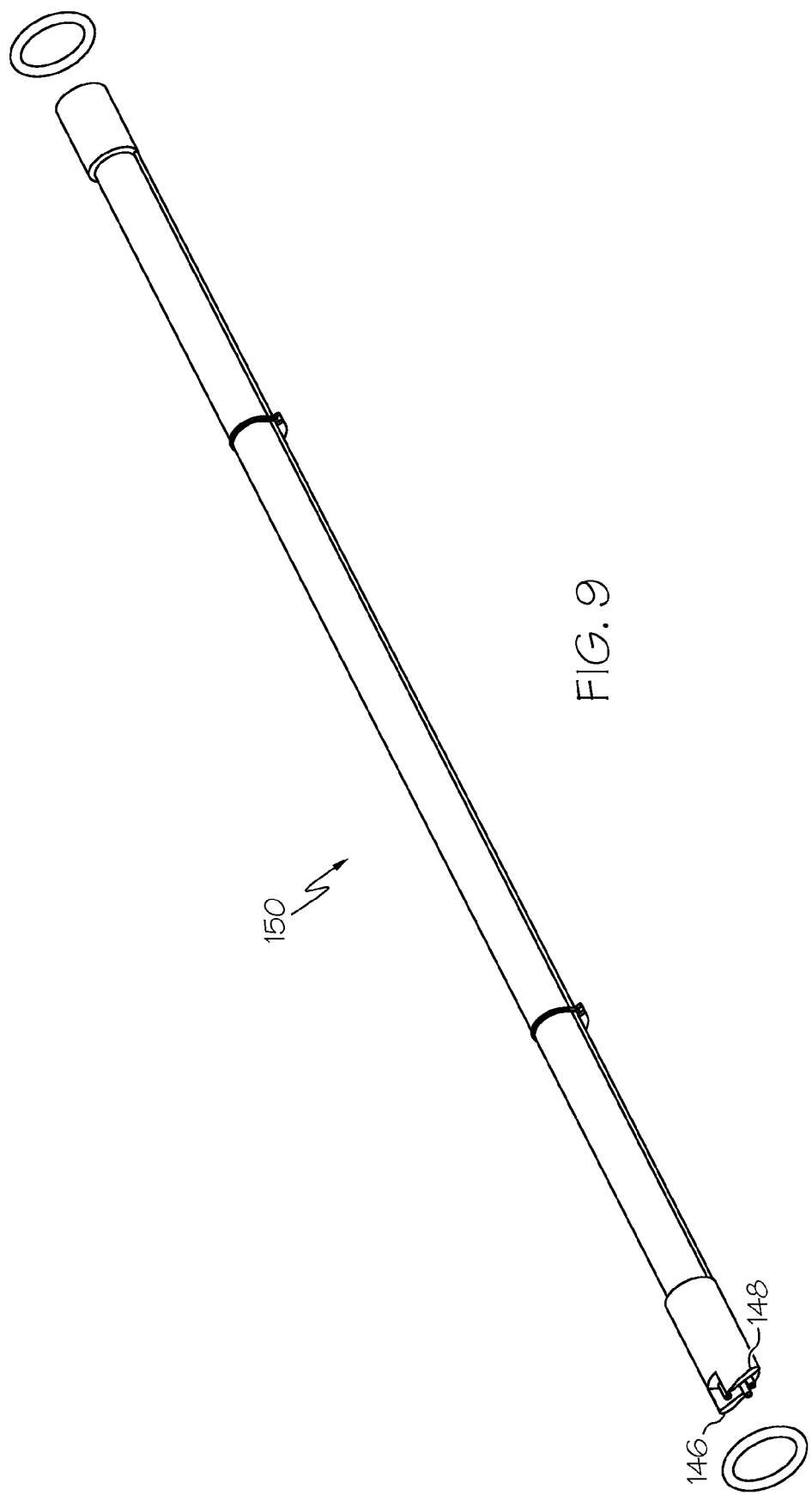
FIG. 9 is a perspective view of a UV lamp for connecting with the lamp head assembly of FIG. 6 according to the present disclosure.
Figure 10:
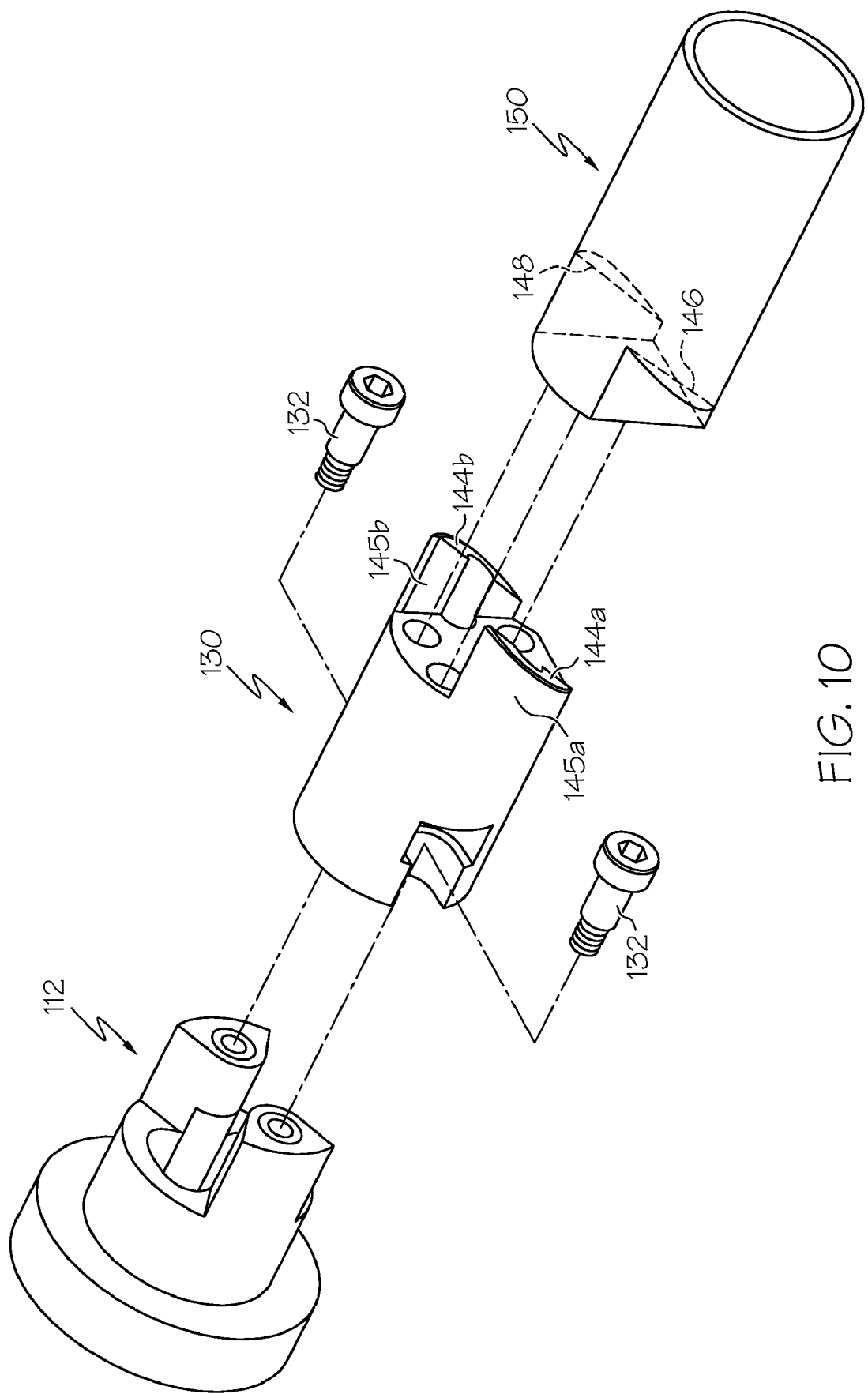
FIG. 10 is an exploded view of a lamp socket having male fork members that engage with recessed socket engaging surfaces of a UV lamp.

Referring to FIG. 9, the lamp engagement surfaces 144a and 144b are oriented to engage socket engaging surfaces 146 and 148 of a UV lamp 150 in a manner similar to that described above. As can be seen, in this embodiment, the socket engaging surfaces 146 and 148 of the UV lamp 150 are on ends of male fork members, which slide into slots adjacent the lamp engagement surfaces 144a and 144b of the lamp socket 130. As an alternative, referring to FIG. 10, this male/female arrangement may be reversed, such that the lamp engagement surfaces 144a and 144b of the lamp socket 130 are at ends of outwardly extending male fork members 145a and 145b, and the socket engaging surfaces 146 and 148 of the UV lamp 150 are recessed. In the embodiment shown in FIG. 10, the lamp socket 130 may be fastened to the second cable gland member 112 using fasteners 132, for example.

For the purposes of describing and defining the present invention it is noted that the terms "substantially" and "approximately" are utilized herein to represent the inherent degree of uncertainty that may be attributed to any quantitative comparison, value, measurement, or other representation. The terms "substantially" and "approximately" are also utilized herein to represent the degree by which a quantitative representation may vary from a stated reference without resulting in a change in the basic function of the subject matter at issue.

Having described the subject matter of the present disclosure in detail and by reference to specific embodiments thereof, it will be apparent that modifications and variations are possible without departing from the scope of the invention defined in the appended claims. For example, the lamp sockets illustrated herein may be provided in any configuration that is suitable for forcing the above-noted rotational orientation. More specifically, the lamp base and lamp socket need not be presented in the mitered form described above. Stepped, keyed, rounded, and other rotationally inhibitive configurations are contemplated. Further, the concepts of the present disclosure also contemplate a variety of alternative means for self-locating the rotation of the lamp, lamp socket, socket base, and assembly mount, and need not be limited to pins, notches, inclined surfaces, etc. Additionally, the UV treatment system 10 may include multiple lamps that have self-locating structures that are the same as or similar to those described above.

What is claimed is:

1. An ultraviolet (UV) water purification system, comprising:
   a flow control structure comprising a first end, a second, opposite end and an elongated axis that passes between the first and second ends, the flow control structure including a UV water purification chamber that receives a fluid during a purification operation;

a lamp mounting assembly configured to mount a UV lamp at least partially within the flow control structure, the lamp mounting assembly comprising:

a mount assembly mounted at the first end of the flow control structure, the mount assembly comprising a conductor housing receiving opening extending therethrough;

a socket base structure including a socket base and a conductor housing extending outwardly from the socket base, the conductor housing received by the conductor housing receiving opening of the mount assembly;

a lamp socket connected to the conductor housing to allow an electrical connection between the lamp socket and a power source, wherein the lamp socket has a mitered lamp engaging surface;

alignment structure to align the socket base structure and the lamp engaging surface at a predetermined rotational orientation about the elongated axis of the flow control structure; and a UV lamp comprising a socket connector having a mitered socket engaging surface, wherein (i) the mitered lamp engaging surface defines a mitered leading edge of the lamp socket, (ii) the mitered socket engaging surface defines a mitered leading edge of the UV lamp, and (iii) the mitered lamp engaging surface and the mitered socket engaging surface define opposite, congruent angles $\theta_1$ and $\theta_2$ to the elongated axis of the flow control structure when the UV lamp is mounted within the flow control structure and force a mounted UV lamp to adopt a fixed rotational orientation about the elongated axis of the flow control structure.

2. The UV water purification system of claim 1, wherein the lamp socket is formed separate from the conductor housing and connected thereto to allow an electrical connection between the lamp socket and the power source.

3. The UV water purification system of claim 1, wherein the lamp socket is formed integrally with the conductor housing.

4. The UV water purification system of claim 1, wherein the lamp socket has multiple mitered lamp engaging surfaces.

5. The UV water purification system of claim 4, wherein the multiple lamp engaging surfaces lie in the same plane.

6. The UV water purification system of claim 1 further comprising a longitudinal wire that runs along a length of an exterior surface of the UV lamp to provide electrical contact with filaments in the UV lamp, wherein the mitered lamp engaging surface and the mitered socket engaging surface cooperate when connecting the socket connector to the lamp socket to automatically align the UV lamp so that the longitudinal wire is located at a predetermined rotational orientation about the elongated axis of the flow control structure.

7. The UV water purification system of claim 1, wherein one of the mitered lamp engagement surface and the mitered socket engagement surface is located at the end of an outwardly extending fork member.

8. A lamp mounting assembly that mounts a UV lamp within a flow control structure comprising an elongated axis, the lamp mounting assembly comprising:

a mount assembly that mounts at an end of the flow control structure, the mount assembly comprising a conductor housing receiving opening extending therethrough;

a socket base structure including a socket base and a conductor housing extending outwardly from the socket base, the conductor housing sized to be received by the conductor housing receiving opening of the mount assembly;

a lamp socket connected to the conductor housing to allow an electrical connection between the lamp socket and a power source, wherein the lamp socket has a mitered lamp engaging surface; and alignment structure to align the socket base structure and the lamp engaging surface at a predetermined rotational orientation about the elongated axis of the flow control structure, wherein the mitered lamp engaging surface (i) defines a mitered leading edge of the lamp socket, (ii) is disposed at an angle $\theta_1$ to the elongate axis if the flow control structure when the UV lamp is mounted within the flow control structure, and (iii) forces a mounted UV lamp to adopt a fixed rotational orientation about the elongated axis of the flow control structure.

9. The lamp mounting assembly of claim 8 further comprising alignment structure comprising a locating pin and a pin-receiving opening sized to receive the pin, the pin-receiving opening extending into at least one of the mount assembly and the socket base structure that receives the pin to align the socket base structure and the mitered lamp engaging surface at a predetermined rotational orientation with respect to the mount assembly.

10. The lamp mounting assembly of claim 8, wherein the lamp socket is formed separate from the conductor housing and connected thereto to allow an electrical connection between the lamp socket and the power source.

11. The lamp mounting assembly of claim 8, wherein the lamp socket is formed integrally with the conductor housing.

12. The lamp mounting assembly of claim 8, wherein the lamp socket has multiple mitered lamp engaging surfaces.

13. The lamp mounting assembly of claim 12, wherein the multiple mitered lamp engaging surfaces lie in the same plane.

14. A UV lamp comprising a socket connector having a mitered socket engaging surface, wherein the mitered socket engaging surface (i) defines a mitered leading edge of the UV lamp, (ii) is disposed an angle $\theta_2$ to the elongated axis of the flow control structure when the UV lamp is mounted within the flow control structure, and (iii) forces a mounted UV lamp to adopt a fixed rotational orientation about the elongated axis of the flow control structure to automatically align the UV lamp so that an amalgam spot of the UV lamp is located approximately at a bottom position of a circular cross-section of the UV lamp.

15. The UV lamp of claim 14, wherein the socket connector has multiple mitered socket engaging surfaces.

16. The UV lamp of claim 15, wherein the multiple mitered socket engaging surfaces lie in the same plane.

17. The UV lamp of claim 14 further comprising a longitudinal wire that runs along a length of an exterior surface of the UV lamp to provide electrical contact with filaments in the UV lamp, wherein the mitered socket engaging surface aligns the UV lamp so that the longitudinal wire is located at a predetermined rotational orientation about the elongated axis of the flow control structure.

* * * * *